(12) United States Patent
Prabhakar et al.

(10) Patent No.: US 9,366,843 B2
(45) Date of Patent: Jun. 14, 2016

(54) IRIS IMAGING APPARATUS AND METHODS FOR CONFIGURING AN IRIS IMAGING APPARATUS

(71) Applicant: DELTA ID INC., Fremont, CA (US)

(72) Inventors: Salil Prabhakar, Fremont, CA (US); Valentine Dvorovkin, Santa Cruz, CA (US)

(73) Assignee: Delta ID Inc., Fremont, DA ( * ) Notice: Subject to any disclaimer, the term of this patent is extended or adjusted under 35 U.S.C. 154(b) by 0 days.

(21) Appl. No.: 14/835,309

(22) Filed: Aug. 25, 2015

(65) Prior Publication Data

US 2015/0362700 A1 Dec. 17, 2015

Related U.S. Application Data

(63) Continuation of application No. PCT/US2014/042838, filed on Jun. 18, 2014.

(60) Provisional application No. 61/836,444, filed on Jun. 18, 2013.

(51) Int. Cl.
*G02B 13/00* (2006.01)
*A61B 3/12* (2006.01)
*G06K 9/00* (2006.01)
*H04N 5/225* (2006.01)
*A61B 5/117* (2016.01)

(52) U.S. Cl.
CPC .......... *G02B 13/0015* (2013.01); *A61B 3/1216* (2013.01); *G06K 9/00604* (2013.01); *G06K 9/00617* (2013.01); *H04N 5/2254* (2013.01); *A61B 5/117* (2013.01)

(58) Field of Classification Search
CPC ................ G11B 2007/24612; G11B 7/00456; G11B 7/00736; G11B 7/246
See application file for complete search history.

(56) References Cited

U.S. PATENT DOCUMENTS

| | | | |
|---|---|---|---|
| 6,289,113 B1 | 9/2001 | McHugh et al. | |
| 7,277,561 B2 | 10/2007 | Shin | |
| 7,761,453 B2 | 7/2010 | Hamza | |
| 8,064,647 B2 | 11/2011 | Bazakos et al. | |
| 8,090,246 B2 | 1/2012 | Jelinek | |
| 8,594,388 B2* | 11/2013 | Mathieu | A61B 3/14 348/77 |
| 2010/0110275 A1* | 5/2010 | Mathieu | A61B 3/14 348/360 |
| 2010/0183199 A1* | 7/2010 | Smith | G06F 19/322 382/117 |

* cited by examiner

*Primary Examiner* — Chikaodili E Anyikire
*Assistant Examiner* — Kehinde O Abimbola
(74) *Attorney, Agent, or Firm* — Hoffmann & Baron, LLP

(57) ABSTRACT

The invention comprises an iris imaging apparatus comprising an image sensor and an optical assembly. The optical assembly comprises an image-side surface and an object-side surface. The optical imaging lens assembly may be configured such that $D1 \leq 6$ mm, $PX_{RES} \geq 10$ pixels per mm, $PX_{SIZE} \leq 1.75$ μm; and $D2 \leq 500$ mm. D1 is a distance between the object-side surface of the optical assembly and the imaging surface. D2 is a maximum distance between the object-side surface of the optical assembly and the object plane. $PX_{RES}$ is pixel resolution in the object plane, achieved by the image sensor in imaging the object plane, when the distance between the object-side surface of the optical assembly and the object plane is less than or equal to D2. $PX_{SIZE}$ is pixel size of the image sensor. The invention additionally includes methods for configuring an imaging apparatus for iris imaging.

25 Claims, 3 Drawing Sheets

TABLE A

| Embodiment | I | II | III | IV | V |
|---|---|---|---|---|---|
| S' (distance between the image-side principal plane of the optical assembly and the image plane) in mm | 5.5 mm | 5.5 mm | 8.7 mm | 5.6 mm | 6.6 mm |
| $PX_{SIZE}$ (pixel size of image sensor) μm | 1.1 μm | 1.75 μm | 1.75 μm | 1.4 μm | 1.4 μm |
| $PX_{Res}$ (pixel resolution in the object plane) in pixels/mm | 10 | 10 | 10 | 10 | 10 |
| Smax (distance between object-side principal plane and object plane) in mm | 500 | 314 | 497 | 400 | 471 |
| f (focal length) in mm | 5.44 | 5.41 | 8.55 | 5.52 | 6.51 |

FIGURE 3

IRIS IMAGING APPARATUS AND METHODS FOR CONFIGURING AN IRIS IMAGING APPARATUS

CROSS-REFERENCES TO RELATED APPLICATIONS

This application is a continuation of PCT Application No. PCT/US2014/042838, filed Jun. 18, 2014, which claims priority to U.S. Provisional Application No. 61/836,444, filed Jun. 18, 2013, the entire contents of these references being incorporated by reference herein.

FIELD OF INVENTION

The invention relates to an imaging apparatus disposed within a mobile device, which imaging apparatus is capable of obtaining images of one or more features of a subject's eye for biometric identification. The invention is particularly operable to obtain images of a subject's iris for iris recognition.

BACKGROUND

Methods for biometric identification based on facial features, including features of the eye are known. Methods for iris recognition implement pattern-recognition techniques to compare an acquired image of a subject's iris against a previously acquired image of the subject's iris, and thereby determine or verify identity of the subject. A digital template corresponding to an acquired iris image is encoded based on the image, using mathematical/statistical algorithms. The digital template is thereafter compared against databases of previously encoded digital templates (corresponding to previously acquired iris images), for locating a match and thereby determining or verifying identity of the subject.

Apparatuses for iris recognition may comprise an imaging apparatus for capturing an image of the subject's iris(es) and an image processing apparatus for comparing the captured image against previously stored iris image information. The imaging apparatus and image processing apparatus may comprise separate devices, or may be combined within a single device.

While iris recognition apparatuses have been previously available as dedicated or stand alone devices, it is increasingly desirable to incorporate iris recognition capabilities into mobile communication devices or mobile computing devices (collectively referred to as "mobile devices") having inbuilt cameras It has however been found that imaging apparatuses or cameras within mobile devices are intended to operate as general purpose cameras, capable of capturing images of objects situated at a wide range of distances from the mobile device. The considerations for acquiring iris images for the purpose of biometric recognition, are significantly different from considerations applicable to image capture of non-iris images, and cameras disposed within mobile devices have been found to be insufficient for the purposes of iris imaging for biometric recognition.

There is accordingly a need for configurations for imaging apparatuses or cameras disposed within mobile devices, which optimize such imaging apparatuses or cameras for iris image acquisition.

SUMMARY

The invention comprises an iris imaging apparatus for acquiring an image of a subject's iris for iris image recognition. The apparatus comprises an image sensor comprising an imaging surface, and an optical assembly interposed between an object plane and the image sensor for imaging the object plane onto the imaging surface, the optical assembly comprising an image-side surface and an object-side surface. Elements of the optical imaging lens assembly may be configured to satisfy the relations:

$D1 \leq 6$ mm;
$PX_{RES} \geq 10$ pixels per mm;
$PX_{SIZE} \leq 1.75$ µm; and
$D2 \leq 500$ mm;

wherein (i) D1 is a distance between the object-side surface of the optical assembly and the imaging surface (ii) D2 is a maximum distance between the object-side surface of the optical assembly and the object plane at which the subject's iris may be positioned for iris image recognition (iii) PX is pixel resolution in the object plane, achieved by the image sensor in imaging the object plane, when the distance between the object-side surface of the optical assembly and the object plane is less than or equal to D2, and (iv) $PX_{SIZE}$ is pixel size of the image sensor.

The iris imaging apparatus may be configured such that $D1 \leq 5$ mm and $D2 \leq 482$ mm. In an embodiment, 200 mm $\leq D2 \leq 500$ mm. Focal length (f) of the optical assembly may be selected such that $f \leq 5.5$ mm. The iris imaging apparatus may be configured such that modulation transfer function (MTF) of the imaging apparatus is greater than or equal to 0.6 at 1 line pair per mm. In an embodiment, image size of an iris imaged at the object plane is greater than or equal to 640×480 pixels.

In a specific embodiment of the invention, the iris imaging apparatus may be configured such that:

$D1 \leq 5.5$ mm;
200 mm $\leq D2 \leq 500$ mm;
$PX_{SIZE} \leq 1.1$ µm;
MTF $\geq 0.6$ at 1 line pairs per mm; and
image size of an iris imaged at the object plane is greater than or equal to 640×480 pixels.

In another specific embodiment of the invention, the iris imaging apparatus may be configured such that:

$D1 \leq 5.6$ mm;
200 mm $\leq D2 \leq 400$ mm;
$PX_{SIZE} \leq 1.4$ µm;
MTF $\geq 0.6$ at 1 line pairs per mm; and
image size of an iris imaged at the object plane is greater than or equal to 640×480 pixels.

The optical assembly of the iris imaging apparatus may be a fixed focus optical assembly. The image sensor and at least the image-side optical surface of the optical assembly may be housed within a mobile device housing. Preferable, the image sensor and the optical assembly may be housed within a mobile device housing.

In an embodiment, D1 may be less than or equal to thickness of the mobile device housing. In a more specific embodiment, thickness of the mobile device housing is less than or equal to 11 mm.

The invention additionally includes methods for configuring an iris imaging for acquiring an image of a subject's iris for iris image recognition, by implementing one or more of the configurations discussed immediately hereinabove.

BRIEF DESCRIPTION OF THE ACCOMPANYING DRAWINGS

FIG. 3 illustrates configuration parameters for embodiments of the iris imaging apparatus of the present invention.

DETAILED DESCRIPTION

Figure 1:
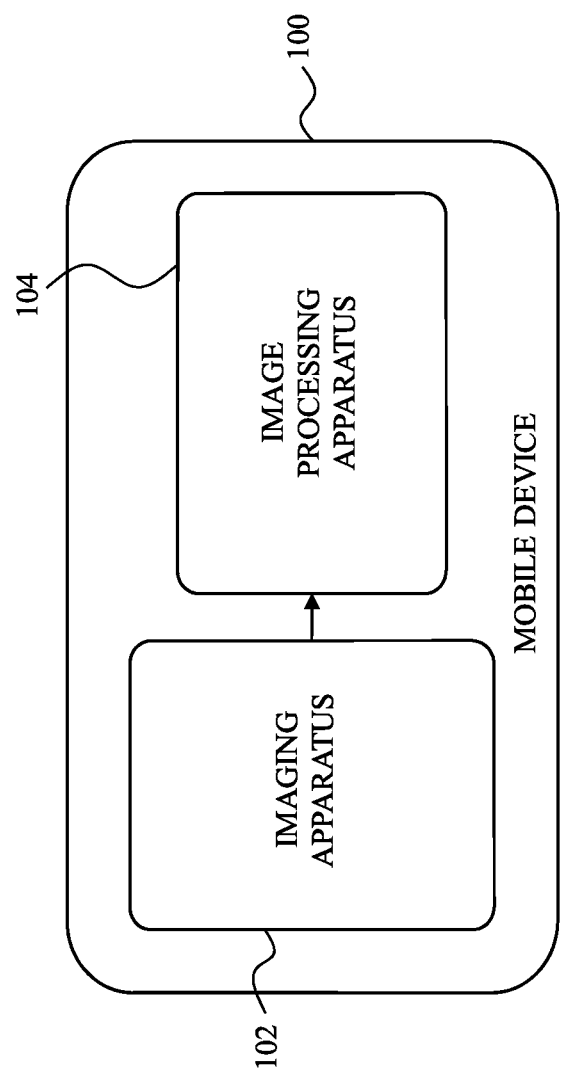
FIG. 1 is a functional block diagram of a mobile device configured for iris image based recognition.

FIG. 1 is a functional block diagram of a mobile device 100 configured for iris image based recognition, comprising an imaging apparatus 102 and an image processing apparatus 104. Imaging apparatus 102 acquires an image of the subject's iris and transmits the image to image processing apparatus 104. The image captured by imaging apparatus 102 may be a still image or a video image. Image processing apparatus 104 thereafter analyses the acquired image frame(s) and compares the corresponding digital feature set with digital templates encoded and stored based on previously acquired iris images, to identify the subject, or to verify the identity of the subject.

Although not illustrated in FIG. 1, mobile device 100 may include other components, including for extracting still frames from video images, for processing and digitizing image data, for enrolment of iris images (the process of capturing, and storing iris information for a subject, and associating the stored information with that subject) and comparison (the process of comparing iris information acquired from a subject against information previously acquired during enrolment, for identification or verification of the subject's identity), and for enabling communication between components of the mobile device. The imaging apparatus, image processing apparatus and other components of the mobile device may each comprise separate devices, or may be combined within a single mobile device.

In implementing iris recognition apparatuses into mobile devices, it has been discovered that the imaging apparatus requires to comply with one or more of the following five system constraints:

Constraint 1—Minimum Pixel Resolution in Object Plane: for iris image capture, the minimum pixel resolution in the object plane $PX_{Res}$ is required to satisfy the condition:

$PX_{Res} \geq 10$ pixels per mm

Constraint 2—Modulation Transfer Function (MTF): Modulation transfer function (MTF) approximates the position of best focus for an infrared imaging system, and for iris imaging:

MTF≥60% at 1 line pair per mm

Constraint 3—Image Size: The standard image size $Image_{SIZE}$ for iris image capture is required to satisfy the condition:

$Image_{SIZE} \geq 640 \times 480$ pixels

Constraint 4—Pixel Size: Based on the state of art existing for commercially available image sensors, particularly those used in mobile device cameras, the minimum pixel size $PX_{SIZE}$ is:

$PX_{SIZE} \leq 1.75$ μm (i.e. $1.75 \times 10^{-3}$ mm)

Constraint 5—System Thickness: The term "system thickness" refers to the distance between the image plane (which coincides with an imaging surface of an image sensor) and an object-side optical surface of the camera lens assembly. Since the imaging apparatus is required to fit entirely (or at least substantially within a mobile device having a narrow depth profile, the system thickness T is:

$T \leq 6$ mm (preferably $T \leq 5$ mm)

While the imaging apparatus may be configured to comply with one or more of the following five system constraints, in a preferred embodiment it may be configured to comply with at least constraints 1 and 5, and in another preferred embodiment it may be configured to comply with all of constraints 1 to 5.

Figure 2:
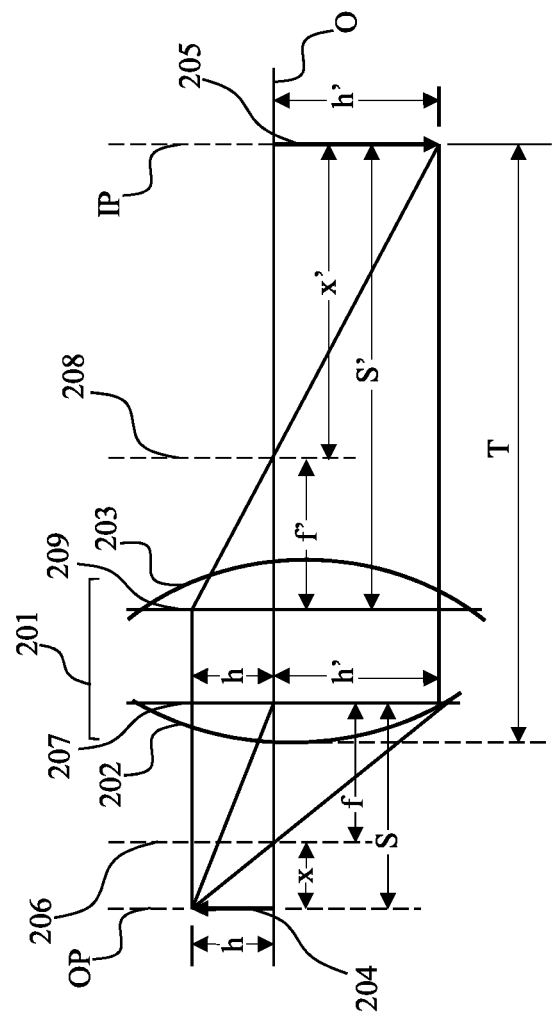
FIG. 2 illustrates cardinal planes of an iris imaging apparatus.

For the purposes of explaining the configurations for an imaging apparatus in accordance with the present invention, FIG. 2 illustrates various cardinal planes of an iris imaging apparatus. The illustration of FIG. 2 comprises an optical assembly 201 interpositioned between object plane OP and image plane IP, such that for an object 204 positioned at object plane OP, an in-focus image 205 is formed at image plane IP.

Optical assembly 201 may be configured and positioned such that image plane IP coincides with an imaging surface of an image sensor within the imaging apparatus. In the illustrated embodiment, optical assembly 201 comprises an object-side surface 202, and an image-side surface 203. Cardinal planes of optical assembly 201 include an object-side focal plane 206, an object-side principal plane 207, and an image-side focal plane 208 and an image-side principal plane 209.

For the purposes of this invention, in accordance with paraxial approximation, it is understood that the term "focal plane" refers to a plane where incident rays parallel to an optical axis of a lens assembly would converge at a point. The term "principal plane" refers to a plane where each incident ray parallel to an optical axis of a lens assembly intersects with a corresponding ray exiting the lens assembly.

It would be understood that optical assembly 201 may comprise a unitarily formed optical element, or may comprise a plurality of discrete optical elements.

In the iris imaging apparatus illustrated in FIG. 2:

h=object size h'=image size

S=distance between object-side principal plane 207 and object plane OP

S'=distance between image-side principal plane 209 and image plane IP f=f'=focal length (which is the distance between object-side principal plane 207 and object-side focal plane 206, and is also the distance between image-side principal plane 209 and image-side focal plane 208)

T=system thickness (i.e. distance between image plane IP and object-side surface 202 of optical lens assembly 201)

In accordance with the iris imaging system of FIG. 2, the absolute value of system magnification M may be calculated as:

$$M = \frac{h'}{h} = \frac{f}{S - f}$$

It accordingly follows that:

$$S = f\left(1 + \frac{1}{M}\right)$$

For a specific pixel resolution in the object plane $PX_{RES}$ (see Constraint 1) and a pixel size $PX_{SIZE}$ (see Constraint 4), an absolute value of magnification M of the system therefore requires to be greater than or equal to $M_{MIN}$ (i.e. $M \geq M_{MIN}$), where:

$$M_{MIN} = PX_{RES} \times PX_{SIZE}$$

By way of example, for an imaging system having a pixel size 1.75 µm and where the minimum pixel resolution in the object plane is 10 pixels/mm, the minimum absolute value of magnification $M_{MIN}$ will be 0.00175×10 i.e. $M_{MIN}$=0.0175 and actual magnification for the purposes of iris recognition requires to be greater or equal than this value of $M_{MIN}$.

For a required absolute value of Magnification M, the maximum permissible distance between the front principal plane and the object plane $S_{max}$ may be arrived at by:

$$Smax = f\left(1 + \frac{1}{M}\right)$$

Accordingly to achieve a magnification having an absolute value greater or equal than the minimum absolute value of magnification $M_{MIN}$, the distance S between the front principal plane and the object plane requires to be such that:

$$S \leq S_{max}$$

Taking the example of an imaging system where focal length f of the lens assembly is 5 mm, $$S_{max} = 5\text{ mm} \times (1 + 1/0.0175) = 291\text{ mm}$$

and actual distance S between the front principal plane and the object plane would require to be less than or equal to this value of $S_{max}$.

In the event the distance S between the front principal plane and the object plane is greater than $S_{max}$, the image acquired by the imaging apparatus would fail to satisfy the required pixel resolution of 10 pixels/mm.

Accordingly, to achieve all of constraints 1 to 5 described above, the invention defines a maximum distance $S_{max}$ between an object-side principal plane of the imaging apparatus lens assembly and an object plane disposed within an image capture region, at which a subject's eye is required to be positioned for iris image capture—such that when positioned at the object plane (or in the vicinity of said object plane), the image of the subject's iris formed on the image sensor satisfies the pixel resolution constraint for iris image recognition.

In an embodiment of the above, the invention provides a method for configuring a mobile device for iris image acquisition—the mobile device having at least one of an image sensor and an optical assembly at least partially disposed within the mobile device housing. One or more of the image sensor, optical assembly and mobile device housing may be positioned to ensure a first distance (D1) between an image plane on the image sensor and an object-side surface of the optical assembly. The configuration of the mobile device is selected to ensure that D1≤6 mm. It will be understood that D1 is required to be limited to ensure that the mobile camera image sensor and optical assembly can be placed substantially (and preferably entirely) within the mobile device housing. The mobile device camera may thereafter be configured to ensure that the object plane intended for iris image acquisition is separated from the object-side surface of the optical assembly by a second distance D2, such that D2≤500 mm.

In an embodiment, the imaging apparatus is configured for iris image capture at a distance less than or equal to $S_{max}$.

In accordance with the above disclosed methods for configuring a mobile device for iris image capture, Table A (shown in FIG. 3) provides parameter data for exemplary embodiments of mobile device imaging apparatuses, configured for iris image capture for the purpose of biometric recognition, in accordance with the methods discussed above.

FIG. 3 illustrates the relationship between S' (distance between the image-side principal plane of the optical assembly and the image plane), $S_{max}$ (distance between object-side principal plane and object plane), $PX_{SIZE}$ (pixel size of image sensor), $PX_{Res}$ (pixel resolution in the object plane) in pixels/mm, and f (focal length), such that in working embodiments, the combination of these variables ensures that at least constraints 1 and 5 (and preferably all of constraints 1 to 5) discussed above are satisfied.

Based on the above, it has been discovered that an iris imaging apparatus comprising (i) an image sensor comprising an imaging surface and (ii) an optical assembly comprising an image-side surface and an object-side surface, and interposed between an object plane and the image sensor for imaging the object plane onto the imaging surface, the optical assembly comprising an image-side surface and an object-side surface, may be configured for optimizing iris imaging capabilities by satisfying the relations:

D1≤6 mm;
$PX_{RES}$≥10 pixels per mm;
$PX_{SIZE}$≤1.75 µm; and
D2≤500 mm;

wherein (i) D1 is a distance between the object-side surface of the optical assembly and the imaging surface, (ii) D2 is a maximum distance between the object-side surface of the optical assembly and the object plane at which the subject's iris may be positioned for iris image recognition, (iii) $PX_{RES}$ is pixel resolution in the object plane, achieved by the image sensor in imaging the object plane, when the distance between the object-side surface of the optical assembly and the object plane is less than or equal to D2 and (iv) $PX_{SIZE}$ is pixel size of the image sensor.

In a particularly advantageous embodiment, the iris imaging apparatus may be configured such that D1≤5 mm and D2≤500 mm. More specifically, the iris imaging apparatus may be configured such that 200 mm≤D2≤500 mm.

Focal length (f) of the optical assembly within the imaging apparatus may be selected such that f≤5.5 mm. The imaging apparatus may be configured such that modulation transfer function (MTF) of the imaging apparatus is greater than or equal to 0.6 at 1 line pairs per mm. In an embodiment, image size of an iris imaged at the object plane may be greater than or equal to 640×480 pixels.

In a specific embodiment, the iris imaging apparatus may be configured for optimizing iris imaging capabilities by satisfying the relations:

D1≤5.5 mm;
200 mm≤D2≤500 mm;
$PX_{SIZE}$≤1.1 µm;
MTF≥0.6 at 1 line pair per mm;

and wherein image size of an iris imaged at the object plane is greater than or equal to 640×480 pixels.

In another embodiment, the iris imaging apparatus may be configured for optimizing iris imaging capabilities by satisfying the relations:

D1≤5.6 mm;
200 mm≤D2≤400 mm;
$PX_{SIZE}$≤1.4 µm;
MTF≥0.6 at 1 line pair per mm;

and wherein image size of an iris imaged at the object plane is greater than or equal to 640×480 pixels.

In an embodiment of the invention, the optical assembly within the iris imaging apparatus may comprise a fixed focus optical assembly. The image sensor and at least the image-side surface of the optical assembly may be housed within a mobile device housing. Preferably, the image sensor and the entire optical assembly may be housed within a mobile device housing. In a preferred embodiment, D1 (i.e. distance between the image plane on the image sensor and the object-side surface of the optical assembly) may be less than or equal to a thickness of the mobile device housing. In an embodiment of this type, the thickness of the mobile device housing be less than or equal to 11 mm.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims.

The invention claimed is:

1. An imaging apparatus for acquiring an image of a subject's iris for iris image recognition, the imaging apparatus comprising:
    an image sensor comprising an imaging surface; and
    an optical assembly interposed between an object plane and the image sensor for imaging the object plane onto the imaging surface, the optical assembly comprising an image-side surface and an object-side surface;
    wherein the imaging apparatus is configured to satisfy the relations:
    $D1 \leq 6$ mm;
    $PX_{RES} \geq 10$ pixels per mm;
    $PX_{SIZE} \leq 1.75$ µm; and
    $D2 \leq 500$ mm;
    and wherein:
    D1 is a distance between the object-side surface of the optical assembly and the imaging surface;
    D2 is a distance between the object-side surface of the optical assembly and the object plane, such that the absolute value of image magnification (M) corresponding to an imaged object positioned at the object plane is greater or equal to $M_{MIN}$, wherein:

$$M_{MIN} = PX_{RES} \times PX_{SIZE};$$

$PX_{RES}$ is pixel resolution in the object plane, achieved by the image sensor in imaging the object plane; and
    $PX_{SIZE}$ is pixel size of the image sensor.

2. The imaging apparatus as claimed in claim 1, wherein $D1 \leq 5$ mm and $D2 \leq 500$ mm.

3. The imaging apparatus as claimed in claim 1, wherein $200$ mm $\leq D2 \leq 500$ mm.

4. The imaging apparatus as claimed in claim 1, wherein focal length (f) of the optical assembly is selected such that:
    $f \leq 5.5$ mm.

5. The imaging apparatus as claimed in claim 1, wherein modulation transfer function (MTF) of the imaging apparatus is greater than or equal to 0.6 at 1 line pair per mm.

6. The imaging apparatus as claimed in claim 1, wherein image size of an iris imaged at the object plane is greater than or equal to 640×480 pixels.

7. The imaging apparatus as claimed in claim 1, wherein:
    $D1 \leq 5.5$ mm;
    $200$ mm $\leq D2 \leq 500$ mm;
    $PX_{SIZE} \leq 1.1$ µm;
    $MTF \geq 0.6$ at 1 line pairs per mm; and
    image size of an iris imaged at the object plane is greater than or equal to 640×480 pixels.

8. The imaging apparatus as claimed in claim 1, wherein:
    $D1 \leq 5.6$ mm;
    $200$ mm $\leq D2 \leq 400$ mm;
    $PX_{SIZE} \leq 1.4$ µm;
    $MTF \geq 0.6$ at 1 line pairs per mm; and
    image size of an iris imaged at the object plane is greater than or equal to 640×480 pixels.

9. The imaging apparatus as claimed in claim 1, wherein the optical assembly is a fixed focus optical assembly.

10. The imaging apparatus as claimed in claim 1, wherein the image sensor and at least the first optical surface of the optical assembly are housed within a mobile device housing.

11. The imaging apparatus as claimed in claim 1, wherein the image sensor and the optical assembly are housed within a mobile device housing.

12. The imaging apparatus as claimed in claim 9, wherein $D1 \leq$ thickness of the mobile device housing.

13. The imaging apparatus as claimed in claim 11, wherein the thickness of the mobile device housing is less than or equal to 11 mm.

14. A method for configuring an imaging apparatus for acquiring an image of a subject's iris for iris image recognition, the imaging apparatus comprising an image sensor comprising an imaging surface, and an optical assembly interposed between an object plane and the image sensor for imaging the object plane onto the imaging surface, wherein the optical assembly comprises an image-side optical surface and an object-side optical surface, the method comprising:
    configuring the imaging apparatus to satisfy the relations:
    $D1 \leq 6$ mm;
    $PX_{RES} \geq 10$ pixels per mm;
    $PX_{SIZE} \leq 1.75$ µm; and
    $D2 \leq 500$ mm;
    wherein:
    D1 is a distance between the object-side surface of the optical assembly and the imaging surface;
    D2 is a distance between the object-side surface of the optical assembly and the object plane, such that the absolute value of image magnification (M) corresponding to an imaged object positioned at the object plane is greater than or equal to $M_{MIN}$, wherein:

$$M_{MIN} = PX_{RES} \times PX_{SIZE};$$

$PX_{RES}$ is pixel resolution in the object plane, achieved by the image sensor in imaging the object plane; and
    $PX_{SIZE}$ is pixel size of the image sensor.

15. The method as claimed in claim 14, wherein $D1 \leq 5$ mm and $D2 \leq 500$ mm.

16. The method as claimed in claim 14, wherein $200$ mm $\leq D2 \leq 500$ mm.

17. The method as claimed in claim 14, wherein focal length (f) of the optical assembly is selected such that:
    $f \leq 5.5$ mm.

18. The method as claimed in claim 14, wherein the image sensor and optical assembly are configured and positioned such that modulation transfer function $(MTF) \geq 0.6$ at 1 line pair per mm.

19. The method as claimed in claim 14, comprising housing the image sensor and at least the image-side optical surface of the optical assembly within a mobile device housing.

20. The method as claimed in claim 14, comprising housing the image sensor and the optical assembly within a mobile device housing.

21. The method as claimed in claim 19, wherein $D1 \leq$ thickness of the mobile device housing.

22. The method as claimed in claim 21, wherein the thickness of the mobile device housing is less than or equal to 11 mm.

23. The imaging apparatus as claimed in claim 1, wherein:
D1≤5.6 mm;
200 mm≤D2≤400 mm;
$PX_{SIZE}$<1.4 μm;
MTF≥0.6 at 1 line pairs per mm; and
image size of an iris imaged at the object plane is greater than or equal to 640×480 pixels.

24. The method as in claim 14, wherein the imaging apparatus is configured to satisfy the relations:
D1≤5.5 mm;
200 mm≤D2≤500 mm;
$PX_{SIZE}$≤1.1 μm;
MTF≥0.6 at 1 line pairs per mm; and
image size of an iris imaged at the object plane is greater than or equal to 640×480 pixels.

25. The method as claimed in claim 14, wherein the imaging apparatus is configured to satisfy the relations:
D1≤5.6 mm;
200 mm≤D2≤400 mm;
$PX_{SIZE}$<1.4 μm;
MTF≥0.6 at 1 line pairs per mm; and
image size of an iris imaged at the object plane is greater than or equal to 640×480 pixels.

* * * * *